(12) United States Patent
Natarajan et al.

(10) Patent No.: US 10,598,577 B2
(45) Date of Patent: Mar. 24, 2020

(54) PHOTODEGRADABLE SAMPLE COLLECTION SYSTEM AND METHOD

(71) Applicants: General Electric Company, Schenectady, NY (US); University of Akron, Akron, OH (US)

(72) Inventors: Arunkumar Natarajan, Niskayuna, NY (US); John Richard Nelson, Clifton Park, NY (US); Patrick McCoy Spooner, Albany, NY (US); Ralf Lenigk, Schenectady, NY (US); Wei Gao, Clifton Park, NY (US); Kwok Pong Chan, Niskayuna, NY (US); Lakshmi Sireesha Kaanumalle, Niskayuna, NY (US); Abraham Joy, Copley, OH (US); Nicholas Nun, Tallmadge, OH (US)

(73) Assignee: General Electric Company, Schenectady, NY (US)

( * ) Notice: Subject to any disclaimer, the term of this patent is extended or adjusted under 35 U.S.C. 154(b) by 246 days.

(21) Appl. No.: 15/639,511

(22) Filed: Jun. 30, 2017

(65) Prior Publication Data
US 2019/0003940 A1 Jan. 3, 2019

(51) Int. Cl.
| | | |
|---|---|---|
| G01N 1/44 | (2006.01) | |
| C08F 2/48 | (2006.01) | |
| C12N 15/10 | (2006.01) | |
| G01N 33/543 | (2006.01) | |
| C08F 8/50 | (2006.01) | |
| G01N 1/02 | (2006.01) | |

(52) U.S. Cl.
CPC ............ *G01N 1/44* (2013.01); *C08F 2/48* (2013.01); *C08F 8/50* (2013.01); *C12N 15/10* (2013.01); *C12N 15/1006* (2013.01); *G01N 1/02* (2013.01); *G01N 33/54366* (2013.01); *C08L 2203/02* (2013.01); *G01N 2001/028* (2013.01)

(58) Field of Classification Search
None
See application file for complete search history.

(56) References Cited

U.S. PATENT DOCUMENTS

| | | | |
|---|---|---|---|
| 6,057,096 A | 5/2000 | Rothschild et al. | |
| 8,685,747 B2 | 4/2014 | Zenhausern et al. | |
| 8,759,075 B2 | 6/2014 | Morhet et al. | |
| 9,180,196 B2 | 11/2015 | Anseth et al. | |
| 9,359,600 B2 | 6/2016 | Morhet et al. | |
| 2014/0210141 A1* | 7/2014 | Moore ................. | D04H 1/4291 264/465 |
| 2014/0378345 A1 | 12/2014 | Hindson et al. | |
| 2015/0125879 A1 | 5/2015 | Li et al. | |
| 2015/0203810 A1* | 7/2015 | Senyei ................. | C12N 5/0068 435/6.1 |
| 2016/0153999 A1 | 6/2016 | Tibbitt et al. | |

FOREIGN PATENT DOCUMENTS

| | | |
|---|---|---|
| KR | 100921425 B1 | 10/2009 |
| KR | 100952891 A1 | 4/2010 |

OTHER PUBLICATIONS

Ming Ni et al., "Cell Culture on MEMS Platforms: A Review", International Journal of Molecular Sciences, vol. 10, Issue: 12, pp. 5411-5441, 2009.

Marshall et al., "Evaluation of a novel material, Diomics X-Swab™, for collection of DNA.", Forensic Science International Genetics, pp. 192-198, Sep. 2014.

\* cited by examiner

*Primary Examiner* — Kenneth R Horlick
(74) *Attorney, Agent, or Firm* — Eversheds Sutherland (US) LLP

(57) ABSTRACT

A method includes providing a biological sample, providing a sample collection device, wherein the sample collection device includes a sample binding surface including a photodegradable polymer configured to bind the biological sample, contacting the biological sample with the sample binding surface of the sample collection device, and irradiating the sample binding surface and the bound biological sample using light emitted from a light source to initiate degradation of the photodegradable polymer of the sample binding surface to cause release of the biological sample.

8 Claims, 12 Drawing Sheets

Before irradiation    After irradiation

PHEA-NBS

PHEMA-NBS

PHOTODEGRADABLE SAMPLE COLLECTION SYSTEM AND METHOD

GOVERNMENT SPONSORSHIP

This invention was made with government support under contract 2015-DN-BX-K042 awarded by the National Institute of Justice, Office of Justice Programs, U.S. Department of Justice. The government has certain rights in the invention.

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

The subject matter disclosed herein relates to collection of biological samples, and more specifically, to photodegradable systems and methods for collection of trace biological samples.

Extraction of trace biological samples (e.g., DNA) from a region of interest (e.g., crime scene) may involve capture and subsequent release of the biological sample for amplification and analysis. Capture of a trace biological sample may involve binding or absorption of the trace biological sample using a collection device. Examples of typical collection devices include cotton (e.g. cellulose fiber) swabs or pads that can be used to bind the biological sample and carry the sample to a lab for analysis. The biological sample may adhere to the cellulose fibers of the cotton swab or pad. However release of the biological sample from the cotton swab or pad may be cumbersome and may not result in complete yield of the trace biological sample collected.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, a method includes providing a biological sample, providing a sample collection device, wherein the sample collection device includes a sample binding surface including a photodegradable polymer configured to bind the biological sample, contacting the biological sample with the sample binding surface of the sample collection device, and irradiating the sample binding surface and the bound biological sample using light emitted from a light source to initiate degradation of the photodegradable polymer of the sample binding surface to cause release of the biological sample.

In a second embodiment, a sample collection device includes a sample binding surface, wherein the sample binding surface includes a photodegradable polymer configured to bind a biological sample and configured to breakdown into a plurality of polymer pieces, monomer pieces, oligomer pieces, or a combination thereof when exposed to a light.

In a third embodiment, a sample collection kit includes one or more sample collection devices, each including a sample binding surface, wherein the sample binding surface includes a photodegradable polymer configured to bind a biological sample and configured to breakdown into a plurality of polymer pieces, monomer pieces, oligomer pieces, or a combination thereof when exposed to a light, and a solution, wherein the plurality of polymer pieces, monomer pieces, oligomer pieces, or the combination thereof are soluble in the solution.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
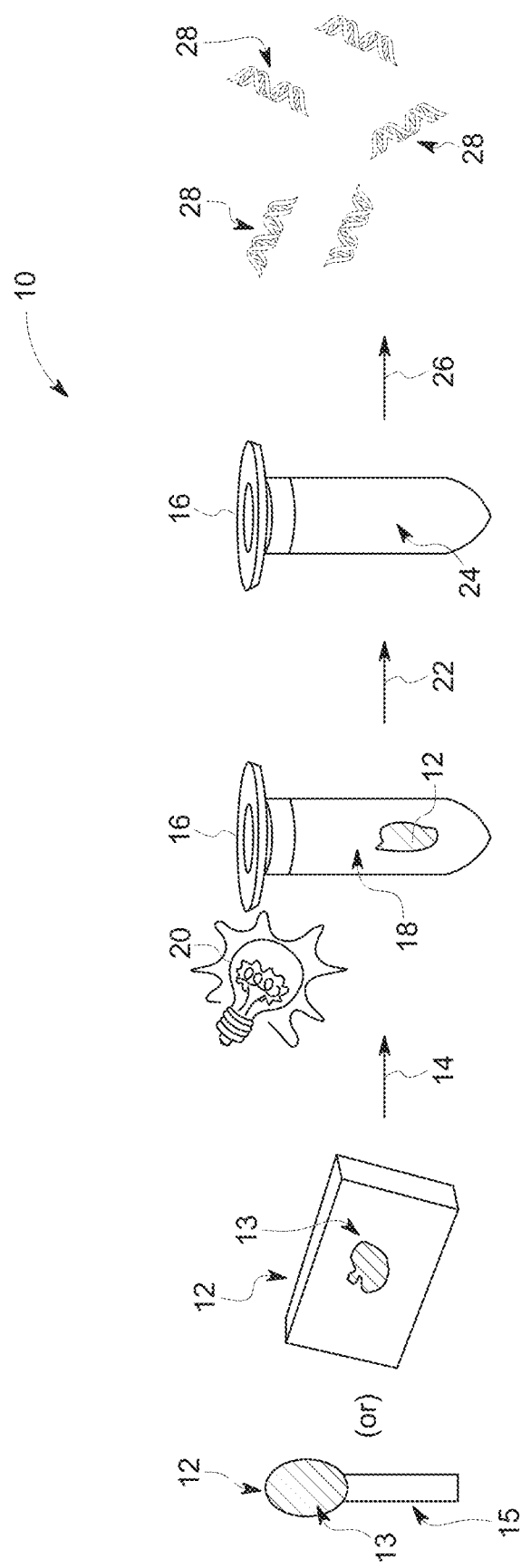
FIG. 1 is a schematic diagram of an embodiment of a method for capture and release of a biological sample using a photodegradable sample collection system, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Biological samples, such as forensic DNA samples, may be found in trace (e.g., low) amounts or concentrations. As noted above, analysis of the trace biological sample may involve capture, release, and amplification of the biological sample (e.g., DNA). The biological sample may be captured in such a way that it can be transported or carried to a lab, or other location, for release, amplification, and/or analysis. Examples of devices that may be used to capture trace biological samples include cotton (e.g., cellulose fiber) swabs and pads. The biological sample may adhere to the cellulose fibers of the cotton swab or pad for transportation, however release of the biological sample from the cotton swab or pad may be cumbersome. Further, release of the biological sample from the cotton swab or pad may result in degradation of the biological sample, and thus, may result in reduced recovery of the trace biological sample collected.

Generally, the disclosed embodiments are directed toward a photodegradable sample collection system, including a photodegradable sample collection device, for capture and release of trace biological samples, and methods of use of the photodegradable sample collection system. A sample binding surface of the photodegradable sample collection device may be made of one or more photodegradable polymers. The photodegradable polymers may bind a biological sample (e.g., cells, DNA, RNA) when interfaced with the biological sample. The photodegradable polymer may include a photodegradable backbone and/or photodegradable moieties that may degrade into monomer and/or oligomer form when exposed to light of particular wavelengths. Further, the polymers, monomers and/or oligomers of the photodegradable polymer may dissolve in solution, thus enabling efficient capture and release of the trace biological sample without degrading the biological sample. Further, in some embodiments, the photodegradable polymer may be water insoluble in polymer form and water soluble in monomer and/or oligomer form, further enabling efficient capture and release of the trace biological sample. Further, in some embodiments, the photodegradable polymer may be water insoluble in polymer form and water soluble in degraded polymer form in which photodegradable moieties have been removed, further enabling efficient capture and release of the trace biological sample. Thus, the photodegradable and photodissolvable sample collection device may enable improved recovery of trace biological samples for analysis. Additionally, the photodegradable sample collection device may take many forms (e.g., swab, pad, brush, paper), thus enabling an increase in the ease of usage of the photodegradable sample collection system for trace biological sample collection.

To illustrate, FIG. 1 shows a schematic diagram of an embodiment of a method 10 for capture and release of a biological sample using a photodegradable sample collection device 12 of the photodegradable sample collection system. The photodegradable sample collection device 12 may be in any form, such as a swab, pad, brush, paper, or any other form suitable for collection of a trace biological sample (e.g., DNA sample, blood sample) 28 from a region of interest, for example from a surface or from an aqueous solution. In the illustrated embodiment, the photodegradable sample collection device 12 is show in a swab form and, alternatively, in a pad form. The photodegradable sample collection device 12 may be used to absorb and capture the biological sample 28 from the region of interest via a sample binding surface 13 of the photodegradable sample collection device 12. The sample binding surface 13 of the photodegradable sample binding system 12 may be made of a photodegradable polymer. The photodegradable polymer may be a polymer susceptible to cleavage or breakdown into small oligomer or monomer pieces upon exposure to particular wavelengths of light. For example, as illustrated, the photodegradable sample collection device 12 may include a handle 15 that permits a user to manipulate sample binding surface 13 without directly contacting/touching the sample binding surface 13. That is, the handle 15 may be plastic or wood, i.e., formed from a material that is not the same material as the sample binding surface 13. In certain embodiments, the handle 15 is relatively rigid and is more rigid than the sample binding surface 13. In other embodiments, the photodegradable sample collection device 12 may be in the form of a strip or generally planar device. In certain embodiments, the sample binding surface 13 may be indicated with printed markers (e.g., a circle, a dot) to direct the user to a particular portion of the photodegradable sample collection device 12. For example, if the photodegradable sample collection device 12 is a paper strip or pad in which only a portion of the device has the sample binding surface 13 (e.g. as a coating or an impregnated material), the portion may be indicated.

Once the biological sample 28 is captured with the photodegradable sample collection device 12, the sample binding surface 13 of the photodegradable sample collection device 12 may be placed in a solution 18 within a reaction vessel 16 (process step 14). The photodegradable sample collection device 12 and the captured biological sample 28 in the solution 18 may be irradiated via a light source 20 at a particular wavelength (e.g., 300-700 nm). The irradiation of the photodegradable sample collection device 12 may cleave photolabile groups (e.g., liable to change or break down in the presence of light) on a backbone of the photodegradable polymer of the sample binding surface 13. This cleavage may release the biological sample 28. After irradiation and cleavage of the photodegradable polymer, the monomers and/or oligomers produced from the cleavage may dissolve in the solution 18 (process step 22) producing a solution 24 having dissolved monomers and/or oligomers of the photodegradable polymer and free unadhered biological sample 28 (e.g., DNA). The free biological sample 28 may then be eluted and isolated from the solution 24 (process step 26).

In certain embodiments, the free biological sample 28 may also be analyzed or provided to downstream techniques, with or without elution or isolation from the solution 24. For example, the free biological sample 28, either isolated or in the solution 24, may be provided as a sample to a DNA sequencing device, a PCR reaction, a hybridization assay, etc.

Figure 2:
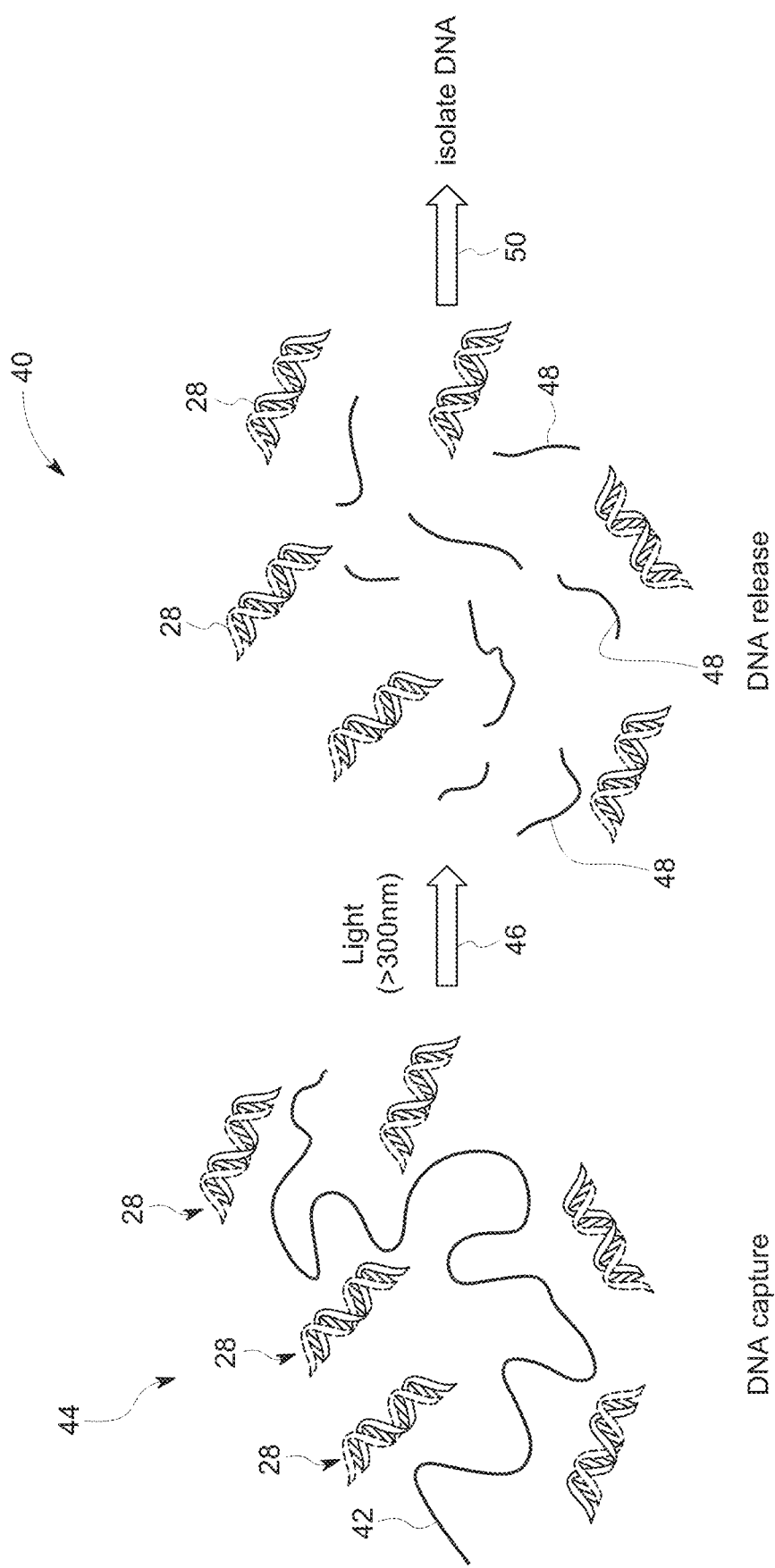
FIG. 2 is a schematic diagram of an embodiment of a method for capture and release of a biological sample using a photodegradable polymer of a photodegradable sample collection system, in accordance with aspects of the present disclosure.

FIG. 2 shows a schematic diagram of an embodiment of a method 40 for capture and release of a biological sample using a photodegradable polymer 42 of the photodegradable sample collection device 12. The photodegradable sample collection device 12 may be used to capture the biological sample 28 from a region of interest. The photodegradable sample collection device 12 may be in any form suitable for collection of a biological sample, such as if the form of a swab, pad, brush, or paper. In some embodiments, the sample binding surface 13 of the photodegradable sample collection device 12 that may interface with the biological sample 28 of interest may make up or cover a portion of the photodegradable sample collection device 12, for example, the sample binding surface may be an end of the photodegradable sample collection device 12. In some embodiments, the sample binding surface 13 may cover or make up the whole of the photodegradable sample collection device 12, such as in embodiments where the photodegradable sample device 12 may be a pad. Thus, the photodegradable sample collection system and/or the sample binding surface 13 of the photodegradable sample collection device 12 may be made of the photodegradable polymer 42. For example, in some embodiments, the whole photodegradable sample collection device 12 may be made of the photodegradable polymer 42, the whole sample binding surface 13 may be made of the photodegradable polymer 42, or the whole photodegradable sample collection device 12 or the sample binding surface 13 may be coated with a coating of the photodegradable polymer 42. In some embodiments, the sample binding surface 13 of the photodegradable polymer 42 may be a coating used to coat a traditional collection device, such as a cotton swab.

The photodegradable polymer 42 may be a polymer that is susceptible to degradation or cleavage upon exposure to light. Additionally, the photodegradable polymer 42 may be a polymer that may adhere to or bind with the biological sample 28 (e.g., DNA) to absorb or capture the biological sample 28 from the region of interest. For example, in some embodiments, the photodegradable polymer 42 may be a cationic polymer such that the photodegradable polymer 42 has a positive charge. This positive charge may enable the photodegradable polymer 42 to adhere or bind to the biological sample 28 when contacted or interfaced with the biological sample 28. Additionally or alternatively, the photodegradable polymer 42 may adhere or bind to the biological sample 28 through hydrogen bonding, or any other suitable adherence technique. In some embodiments, the photodegradable polymer 42 may be a hydrophobic polymer or a combination of one or more hydrophobic polymers. In some embodiments, the photodegradable polymer 42 may be spun via an electrospinning technique to form fibers, and the sample binding surface 13 may be made of the fibers of the photodegradable polymer 42, similar to cotton fibers of a cotton swab or cotton pad. In some embodiments, the electrospun fibers of the photodegradable polymer 42 may have a thickness between 1 nanometer (nm) and 20 micrometers. In some embodiments, the electrospun fibers of the photodegradable polymer 42 may have a thickness between 10 nm and 1,000 nm (1 micrometer).

In the method 40, the sample binding surface 13 made of the photodegradable polymer 42 may be contacted with the biological sample 28. The sample binding surface 13 of the photodegradable sample collection device 12 may capture (e.g., absorb, bind) the biological sample 28 in the manner discussed above (process step 44). Once the biological sample 28 has been captured by the photodegradable polymer 42 of the photodegradable sample collection device 12, the photodegradable sample collection device 12 with the bound biological sample 28 may be transferred to a lab or other location for release and analysis. Next, the sample binding surface 13 of the photodegradable sample collection device 12 and the bound biological sample 28 may be submerged in the solution 18 such that the photodegradable polymer 42 of the sample binding surface 13 and the bound biological sample 28 are surrounded by the solution in the reaction vessel 16.

Next, the reaction vessel 16 containing the solution 18, the photodegradable polymer 42, and the bound biological sample 28 may be exposed to light (process step 46). This irradiation step 46 may be an intense irradiation. The light may be a wavelength that will cleave the pendent groups and/or the backbone of the photodegradable polymer 42. In some embodiments, the wavelength of the light for the irradiation step 46 may be greater than 300 nm, between 300-700 nm, and/or between 350-380 nm. The light may be of such a wavelength that it will not damage the biological sample 28. Further, the intensity of the light needed to degrade the photodegradable polymer 42 and create the cleavage may be high, such that sunlight (e.g., lower intensity ultraviolet light approximately 380 nm) may not cause the photodegradable polymer 42 to degrade quickly unless a very high intensity (energy density) LED's or UV bulbs are used. Thus, the photodegradable sample collection device 12 may be used in the sunlight or ambient artificial light to capture the biological sample 28 without degrading quickly.

Cleavage of the pendent groups and/or the backbone of the photodegradable polymer 42 may create smaller polymer, monomer, and/or oligomer pieces 48 of the photodegradable polymer 42. The cleavage may release the bound biological sample 28, thus creating free unbound biological sample 28. The polymer, monomer, and/or oligomer pieces 48 of the photodegradable polymer 42 may be water soluble such that they may dissolve in the solution 18. In some embodiments, the photodegradable polymer 42 may be water insoluble in polymer form, such that it may not dissolve if capturing the biological sample from an aqueous solution. Further, in some embodiments, as previously mentioned, the photodegradable polymer 42 may be water soluble in cleaved polymer, monomer, and/or oligomer form (e.g., after photocleavage), such that the cleaved polymer, monomer, and/or oligomer pieces 48 of the photodegradable polymer 42 may dissolve in the solution 18 after release of the biological sample 28. The free unbound biological sample 28 may then be isolated from the solution 18 containing the dissolved monomer and/or oligomer pieces of the photodegradable polymer 42. For example, the sample can be treated with a solution to accomplish cell lysis, and the resulting nucleic acid precipitated for downstream use. Alternatively, the resulting sample may be added directly to a subsequent assay, such as DNA fingerprinting analysis (e.g. STR analysis) or DNA sequencing. Thus, the photodegradable and dissolution properties of the photodegradable polymer 42 and the photodegradable sample collection device 12 may enable improved recovery of the trace biological sample 28.

Figure 3A:
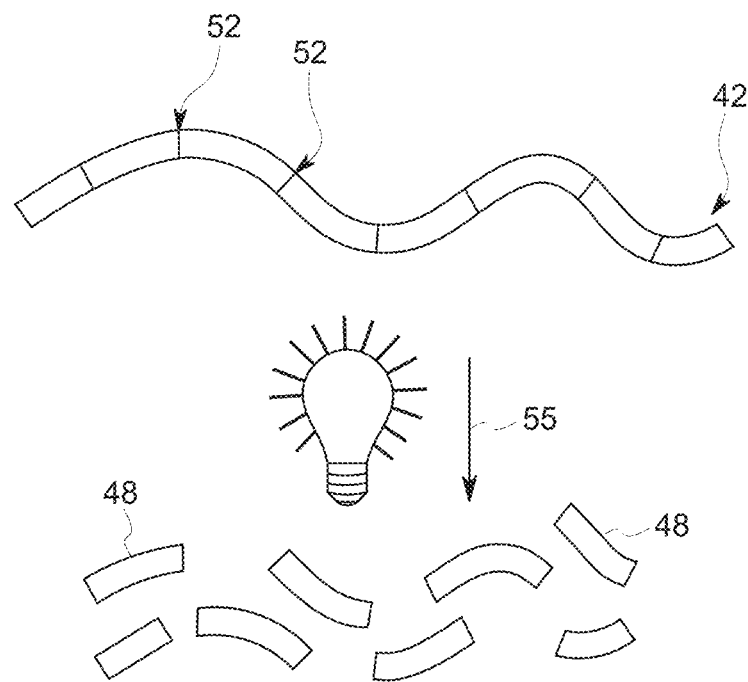
FIGS. 3A and 3B illustrate schematic diagrams of embodiments of the photodegradable polymer 42 and the results of irradiation cleavage of each embodiment of the photodegradable polymer 42, in accordance with aspects of the present disclosure.
Figure 3B:
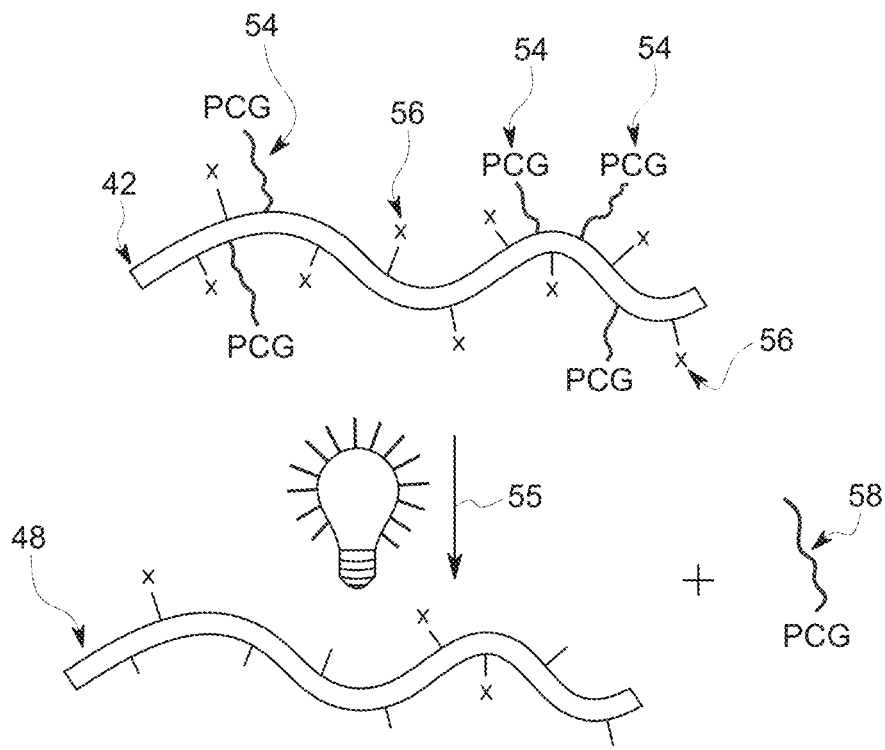

FIGS. 3A and 3B illustrate schematic diagrams of embodiments of the photodegradable polymer 42 and the results of irradiation cleavage of each embodiment of the photodegradable polymer 42. In some embodiments, the photodegradable polymer 42 may include photocleavable moieties 52 as part of the backbone of the photodegradable polymer 42, as shown in FIG. 3A. In some embodiments, the photodegradable polymer 42 may include photocleavable pendant groups 54 (e.g., side groups) attached to the backbone of the photodegradable polymer 42, as shown in FIG. 3B. Each of the embodiments of FIGS. 3A and 3B may be water insoluble in polymer form, and water soluble in cleaved form after irradiation (process step 55).

Examples of the photodegradable polymer 42 include polyhydroxyethyl acrylate (PHEA), polyhydroxyethyl methacrylate (PHEMA) and Polyvinylalcohol surface derivatized (side chains) where the hydroxy groups are appended with Nitrobenzyl succinate groups or trimethoxyphenyl succinate groups. The surface derivatization of the alcohol groups may be 25%, 50%, 75%, 100%, or any percentage between 1% and 100%. In some embodiments, the photodegradable polymer 42 may include photodegradable moieties or pendant groups attached to a water soluble backbone. For example, the photodegradable polymer 42 may include the PHEA or PHEMA conjugated with nitrobenzyl succinate (NBS) as pendant groups. The pendant group may be photodegradable such that it is susceptible to cleavage upon exposure to light. In some embodiments, the photocleavable group may be along the backbone of the photodegradable polymer 42, for example polyester polymer groups functionalized with alkoxyphenacyl photodegradable chromophores.

In FIG. 3A, the photodegradable polymer 42 includes one or more photocleavable moieties 52 included in the backbone of the photodegradable polymer 42. The photocleavable moieties 52 may be the site of cleavage of the backbone of the photodegradable polymer 42 upon irradiation (process step 55). Cleavage of the backbone of the photodegradable polymer 42 may create smaller polymer, monomer, and/or oligomer pieces 48 of the photodegradable polymer 42. The cleavage may release the bound biological sample 28, as previously discussed, thus creating free unbound biological sample 28.

In FIG. 3B, the photodegradable polymer 42 includes one or more photocleavable pendant groups 54 attached as side chains to the backbone of the photodegradable polymer 42. The photocleavable pendant groups 54 may keep the polymer hydrophobic and may be the site of cleavage upon irradiation (process step 55), such that they photocleavable pendant groups are cleaved off of the backbone of the photodegradable polymer. Cleavage of the photodegradable pendant groups 54 may create smaller polymer pieces 48 (e.g., without the photocleavable pendant groups) of the photodegradable polymer 42. The cleavage may release the bound biological sample 28, as previously discussed, thus creating free unbound biological sample 28.

The polymer, monomer, and/or oligomer pieces 48 of the photodegradable polymer 42 may be water soluble such that they may dissolve in the solution 18. In some embodiments, the photodegradable polymer 42 may be water insoluble in polymer form, such that it may not dissolve if capturing the biological sample from an aqueous solution. In some embodiments, as shown in FIG. 3B, the photodegradable polymer 42 may include hydrophilic side chain groups 56, such as hydroxyl groups, that may enable greater wettability of the hydrophobic photodegradable polymer 42. Further, in some embodiments, as previously mentioned, the photodegradable polymer 42 may be water soluble in cleaved polymer, monomer, and/or oligomer form (e.g., after photocleavage), such that the cleaved polymer, monomer, and/or oligomer pieces 48 of the photodegradable polymer 42 may dissolve in the solution 18 after release of the biological sample 28. The unbound biological sample 28 may then be isolated from the solution 18.

Figure 4:
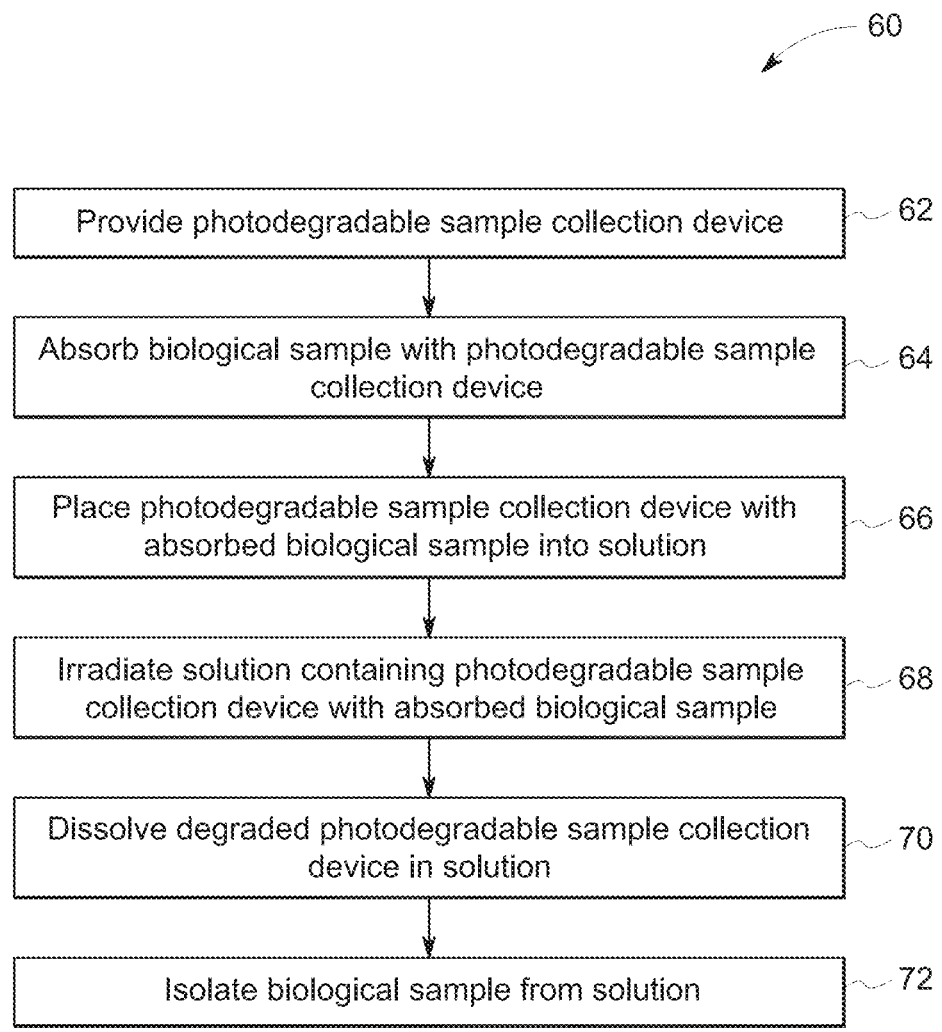
FIG. 4 is a flow diagram of an embodiment of a method for capture and release of a biological sample using a photodegradable sample collection system, in accordance with aspects of the present disclosure.

FIG. 4 is a flow diagram of an embodiment of a method 60 for utilizing the photodegradable sample collection device 12 for the capture and release of the biological sample 28 (e.g., DNA). At a first step 62, the photodegradable sample collection device 12 may be provided. The photodegradable sample collection device 12 may be in any form, such as a swab, pad, brush, paper, or any other form suitable for collection of the biological sample 12. At a next step 64, the trace biological sample 12 may be contacted and absorbed by the sample binding surface 13 of the photodegradable sample collection device 12. As previously discussed, the sample binding surface 13 of the photodegradable sample collection device 12 may be made of the photodegradable polymer 42. The photodegradable polymer 42 may adhere or bind to the biological sample 28 via charge or hydrogen bonding, as previously discussed.

At a next step 66, the photodegradable sample collection device 12 including the absorbed biological sample 28 may be placed into a solution 18 within the reaction tube 16. The photodegradable sample collection device 12 may be positioned such that the photodegradable polymer 42 of the sample binding surface and the absorbed biological sample 28 are submerged in or surrounded by the solution 18. The solution 18 may be water, or any other suitable processing buffer or liquid. In some embodiments, the solution 18 may include a free radical scavenger that may be used to prevent damage to the captured biological sample 28 by byproducts that may be generated during the photodegradable polymer degradation process. At a next step 68, the solution 18 containing the submerged photodegradable polymer 42 and the biological sample 28 may be irradiated using the light source 20. In some embodiments, the wavelength of the light from the light source for the irradiation step 68 may be greater than 300 nm, between 300-700 nm, and/or between 350-380 nm. The light may be of such a wavelength that it will not damage the biological sample 28 (e.g., DNA). The irradiation may cleave the pendant groups and/or the backbone of the photodegradable polymer 42, thus breaking the photodegradable polymer 42 into the smaller monomer and/or oligomer pieces 48. This cleavage may release the absorbed or bound biological sample 28. The photodegradable polymer 42 and the biological sample 28 may be uniformly irradiated to uniformly cleave the photodegradable polymer 42 into the monomer and/or oligomer pieces 48, thus enabling approximately complete release and increased recovery of the biological sample 28.

At a next step 70, the monomer and/or oligomer pieces 48 of the photodegradable polymer 42 may be dissolved into the solution 18. In some embodiments, the photodegradable polymer 42 may be a polymer that is water insoluble in polymer form and water soluble in the monomer and/or oligomer form. In this manner, the photodegradable polymer 42 of the photodegradable sample collection device 12 may enable capture of the biological sample from any region of interest, including an aqueous solution, and may enable increased recovery of the biological sample 28 via dissolution of the monomer and/or oligomer pieces 48 in the solution 18. At a next step 72, the biological sample 28 (e.g., DNA) may be isolated from the solution 18 and the dissolved monomer and/or oligomer pieces 48 of the photodegradable polymer 42. The biological sample 28 may then be amplified, for example by polymerase chain reaction (PCR), and/or analyzed. Thus, the method 60 for catch and release of the trace biological sample 28 utilizing the photodegradable sample collection device 12 may enable increased recovery of the trace biological sample 12 from a region of interest and a decrease in degradation of the trace biological sample 12 in the process.

Figure 5:
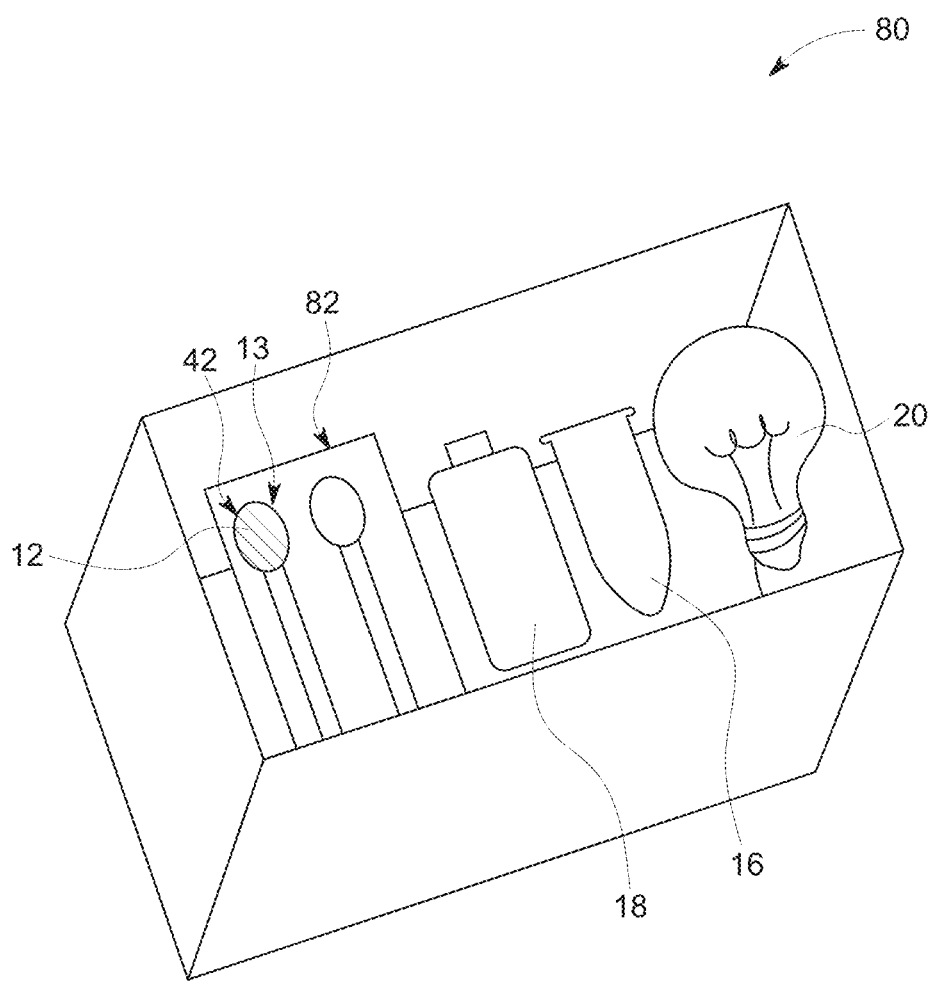
FIG. 5 is a schematic diagram of an embodiment of a photodegradable sample collection kit, in accordance with aspects of the present disclosure.

FIG. 5 illustrates an embodiment of a sample collection kit 80 that may include the instrumentation (e.g., the photodegradable sample collection system) for carrying out one or more of the methods previously discussed. In some embodiments, the sample collection kit 80 for capture and release of a trace biological sample 28 may be provided. The sample collection kit 80 may include one or more of the materials for performing a capture and release of the trace biological sample 28 (e.g., a photodegradable sample collection system). The sample collection kit 80 may include one or more of the photodegradable sample collection device 12. In the illustrated embodiment, the photodegradable sample collection device 12 is in the form of a swab, with the sample binding surface 13 at one end of the photodegradable sample collection device 12. In some embodiments, the one or more photodegradable sample collection device 12 included in the sample collection kit 80 may be in any other form suitable for collection of the biological sample 28, such as a pad or paper. In such embodiments, the sample binding surface 13 may be or cover all or part of the photodegradable sample collection device 12. In some embodiments, within the sample collection kit 80, the one or more photodegradable sample collection device 12 may be packaged in a separate packaging material 82. In some embodiments, the packaging material 82 may be resistant to UV light and/or light in the visible spectrum such that the photodegradable polymer 42 of the photodegradable sample collection device 12 may not degrade if the sample collection kit 80 is used or left in the presence of sunlight.

In some embodiments, the sample collection kit 80 may include the reaction tube 16 and/or the solution 18 into which the photodegradable polymer 42 of the photodegradable sample collection device 12 and the absorbed biological sample 28 may be submerged once the biological sample 28 has been captured. In some embodiments, the solution 18 may be a buffer. In some embodiments, the solution 18 may include the free radical scavenger that may be used to prevent damage to the captured biological sample 28. Additionally, in some embodiments, the sample collection kit 80 may include the light source 20. The light source 20 may be selected to produce light of a particular wavelength, or range of wavelengths that may cleave the photodegradable polymer 42 upon uniform exposure. The wavelength of light produced by the included light source 20 may be greater than 300 nm, between 300-700 nm, and/or between 350-380 nm. In some embodiments, the sample collection kit 80 may include materials for isolating the free biological sample 28 after the biological sample 28 has been released from the photodegradable polymer 42. The sample collection kit 80 may enable increased recovery of the trace biological sample 28.

Figure 6:
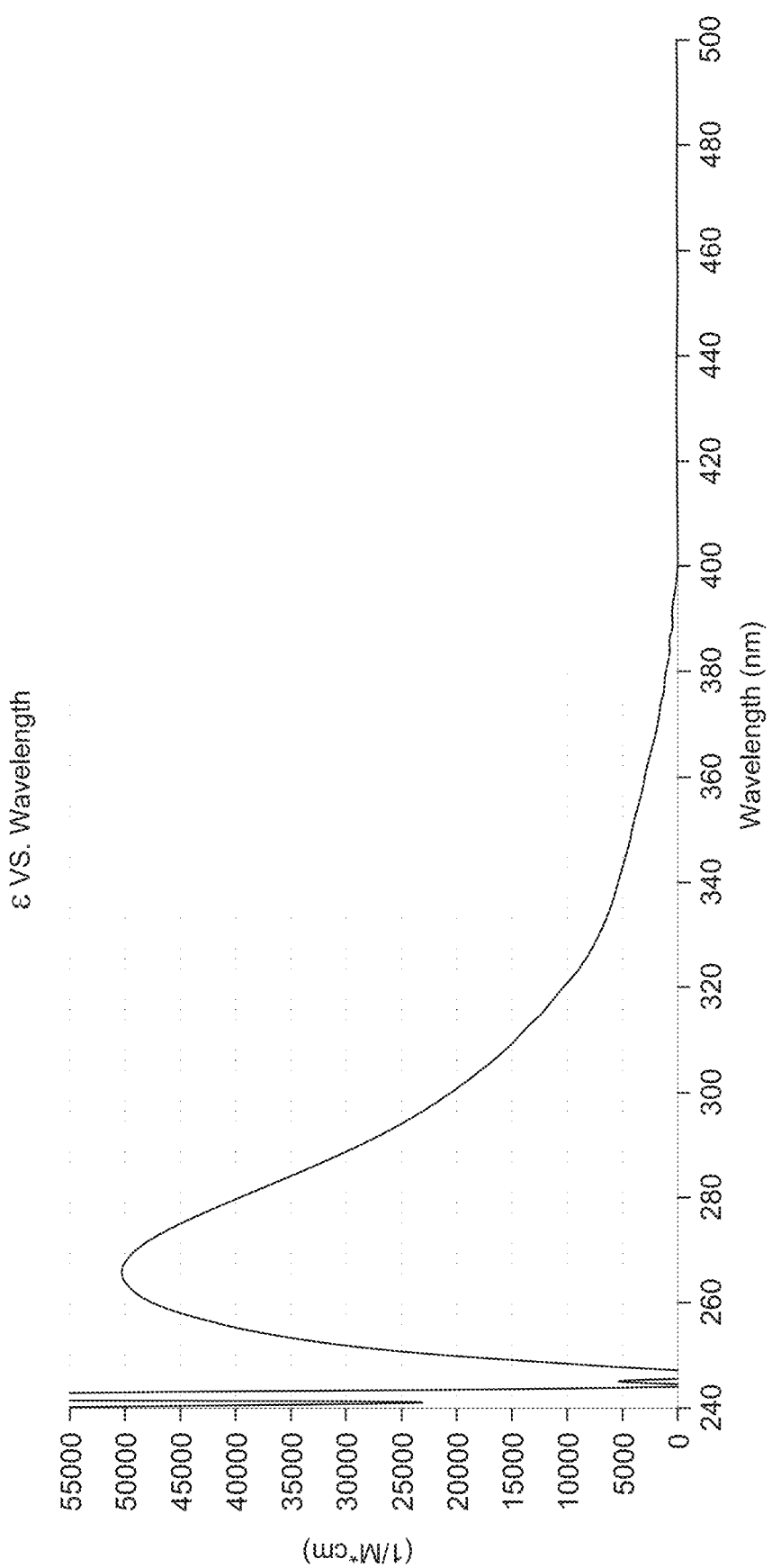
FIG. 6 illustrates an example of a ultraviolet (UV) absorption spectrum of a photodegradable polymer 42, in accordance with aspects of the present disclosure

FIG. 6 illustrates an example of an ultraviolet (UV) absorption spectrum of the photodegradable polymer 42 (e.g., photocleavable polymer). The photodegradable sample collection device 12 and the captured biological sample 28 in the solution 18 may be irradiated via a light source 20 at a particular wavelength (e.g., 300-700 nm). The light may be a wavelength that will cleave the pendent groups and/or the backbone of the photodegradable polymer 42. In some embodiments, the wavelength of the light for the irradiation step 46 may be greater than 300 nm, between 300-700 nm, and/or between 350-380 nm. As shown, the extinction coefficient (e.g., molar absorptivity) of the photodegradable polymer 42 at 365 nm may be 2491$M^{-1}$ $cm^{-1}$.

The light may be of such a wavelength that it will not damage the biological sample 28. Further, the intensity of the light needed to degrade the photodegradable polymer 42 and create the cleavage may be high, such that sunlight (e.g., lower intensity ultraviolet light approximately 380 nm) may not cause the photodegradable polymer 42 to degrade quickly unless a very high intensity (energy density) LED's or UV bulbs are used. Thus, the photodegradable sample collection device 12 may be used in the sunlight or ambient artificial light to capture the biological sample 28 without degrading quickly.

Figure 7A:
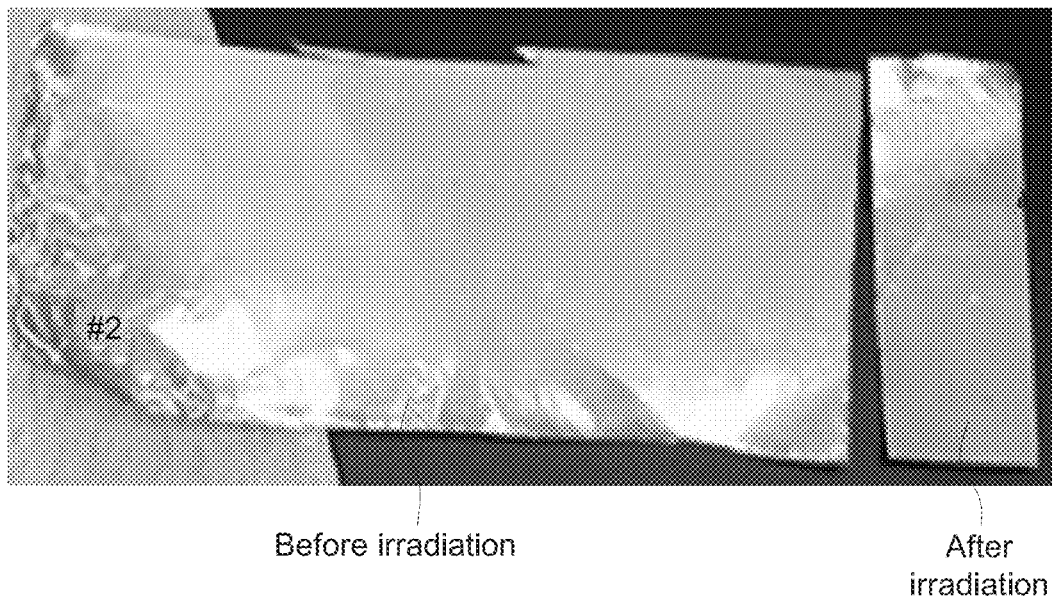
FIGS. 7A and 7B show cleavage of an electrospun photodegradable polymer upon irradiation, in accordance with aspects of the present disclosure.
Figure 7B:
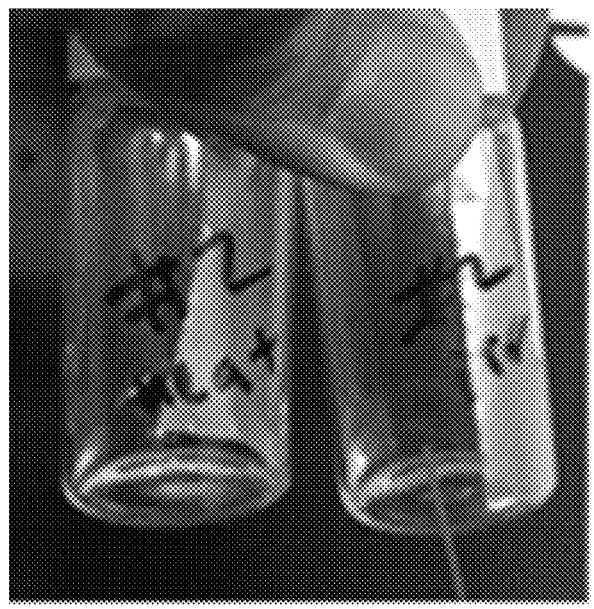

FIGS. 7A and 7B depict images showing cleavage and breakdown of the photodegradable polymer 42, here alkoxyphenacyl polymer, upon irradiation by the light source 20 that has been electrospun on aluminum foil which turns yellow upon light exposure with 365 nm Rayonet reactor for 45 minutes. While 45 minutes of irradiation was used in this instance, cleavage and breakdown of the photodegradable polymer 42 may be achieved by irradiation for increments of time below 45 minutes and above 45 minutes. As previously discussed, the photodegradable polymer 42 may make up the sample binding surface 13 of the photodegradable sample collection device 12 that may be used to capture the trace biological sample 28.

FIG. 7A shows the photodegradable polymer 42 electrospun on aluminum foil. This polymer was made by mixing 500 mg of PHEMA-NBS-100% dissolved into 2 ml of buffer (2:3 dimethylformamide:chloroform), and electrospun using a 22 gauge needle, across a 12 cm gap at 1 ml/hr using 21 KV potential resulting in fibers approximately 1 micron in diameter. Electrospinning of the fibers may enable the fiber width to be narrow (e.g., thin) and uniformly controlled. For example, fibers can quite easily be made 1-2 microns wide or smaller, which allows for rapid dissolution into aqueous solutions upon photodegradation. The fibers may be made to have thicknesses within a range that enables dissolution into solution upon photodegradation. In some embodiments, the electrospun fibers of the photodegradable polymer 42 may have a thickness between 1 nanometer (nm) and 20 micrometers. In some embodiments, the electrospun fibers of the photodegradable polymer 42 may have a thickness between 10 nm and 1,000 nm (1 micrometer).

In this experiment, the submerged photodegradable polymer 42 was irradiated with light of 365 nm. The photodegradable polymer 42 may be water insoluble in polymer form as seen in the left vial in FIG. 7B. Since the polymer 42 is photodegradable, the photodegradable polymer 42 may be susceptible to cleavage or breakdown upon exposure to light of particular wavelengths, as shown in the right vial in FIG. 7B (in this experiment, the degraded photodegradable polymer turned yellow in solution upon irradiation). The right vial shows the photodegradable polymer after it has been cleaved by the light into the smaller degraded components (e.g., smaller polymer, monomer, and/or oligomer pieces 48) and has begun to dissolve into the solution 18. Thus, as shown in the right vial, the cleaved underlying base polymer becomes soluble and may swell in the solution, liberating the biological sample. This cleavage and dissolution of the photodegradable polymer 42 upon irradiation at a particular wavelength, or range of wavelengths, may enable increased recovery of the trace biological sample 28 that may be captured using the photodegradable polymer 42 of the photodegradable sample collection device 12.

Figure 8:
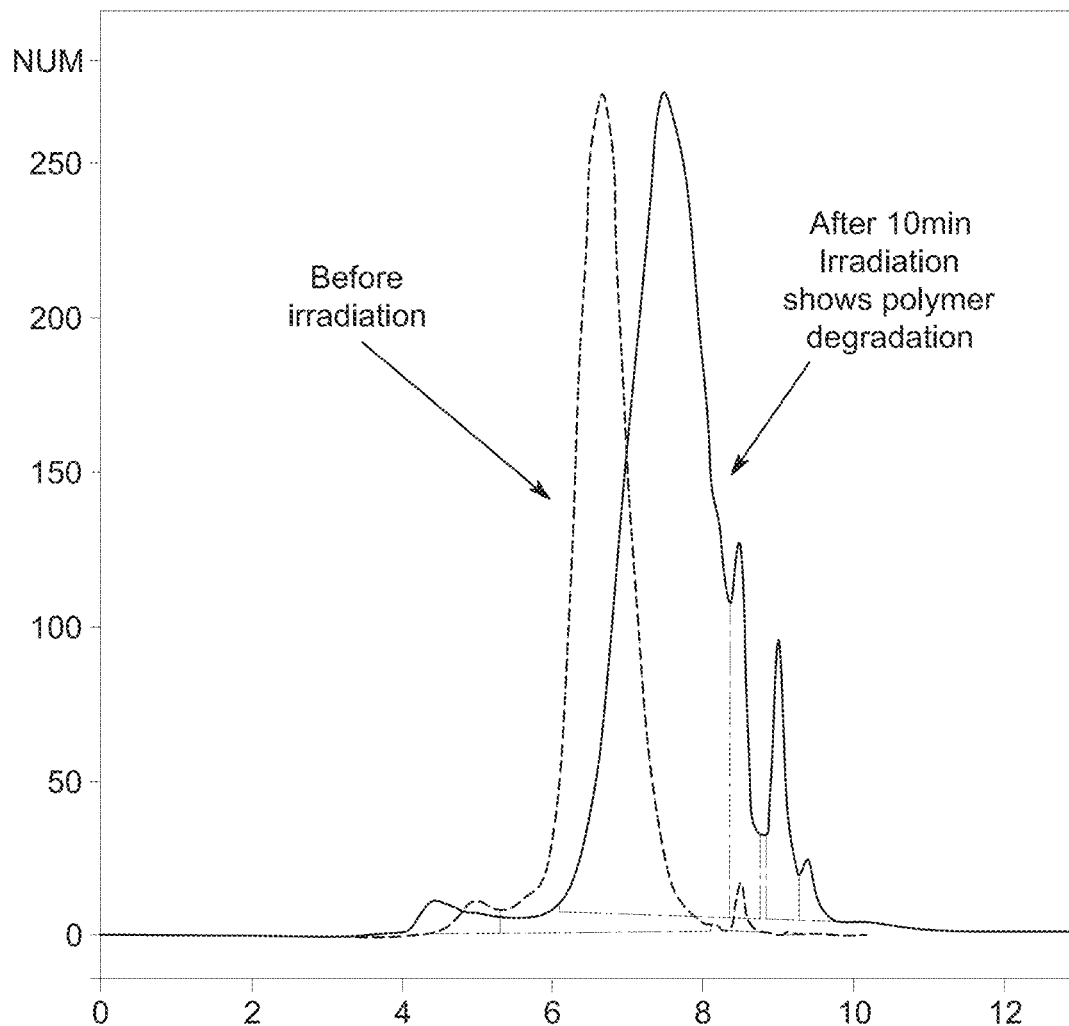
FIG. 8 is a graph showing photodegradable polymer degradation after irradiation, in accordance with aspects of the present disclosure.

FIG. 8 is a graph that shows gel permeation chromatography (GPC) results illustrating degradation of the photodegradable polymer 42 after 10 minute irradiation in an Omnicure photoreactor at 300 nm. The left spike on the graph illustrates the photodegradable polymer 42 in polymer form before irradiation by the light source 20 having a molecular weight of approximately 35 kDa. The right spike on the graph illustrates the monomer and/or oligomer pieces 48 of the photodegradable polymer 42 after 10 mins of irradiation by the light source 20 having an average molecular weight less than 5 kDa. As previously discussed, irradiation of the photodegradable polymer 42 of the photodegradable sample collection device 12 may cleave the pendent groups and/or the backbone of the photodegradable polymer 42 producing the smaller monomer and/or oligomer pieces 48 of the photodegradable polymer 42. This cleavage of the photodegradable polymer 42 upon irradiation at a particular wavelength, or range of wavelengths, may enable increased recovery of the trace biological sample 28 that may be captured using the photodegradable polymer 42 of the photodegradable sample collection device 12.

Figure 9:
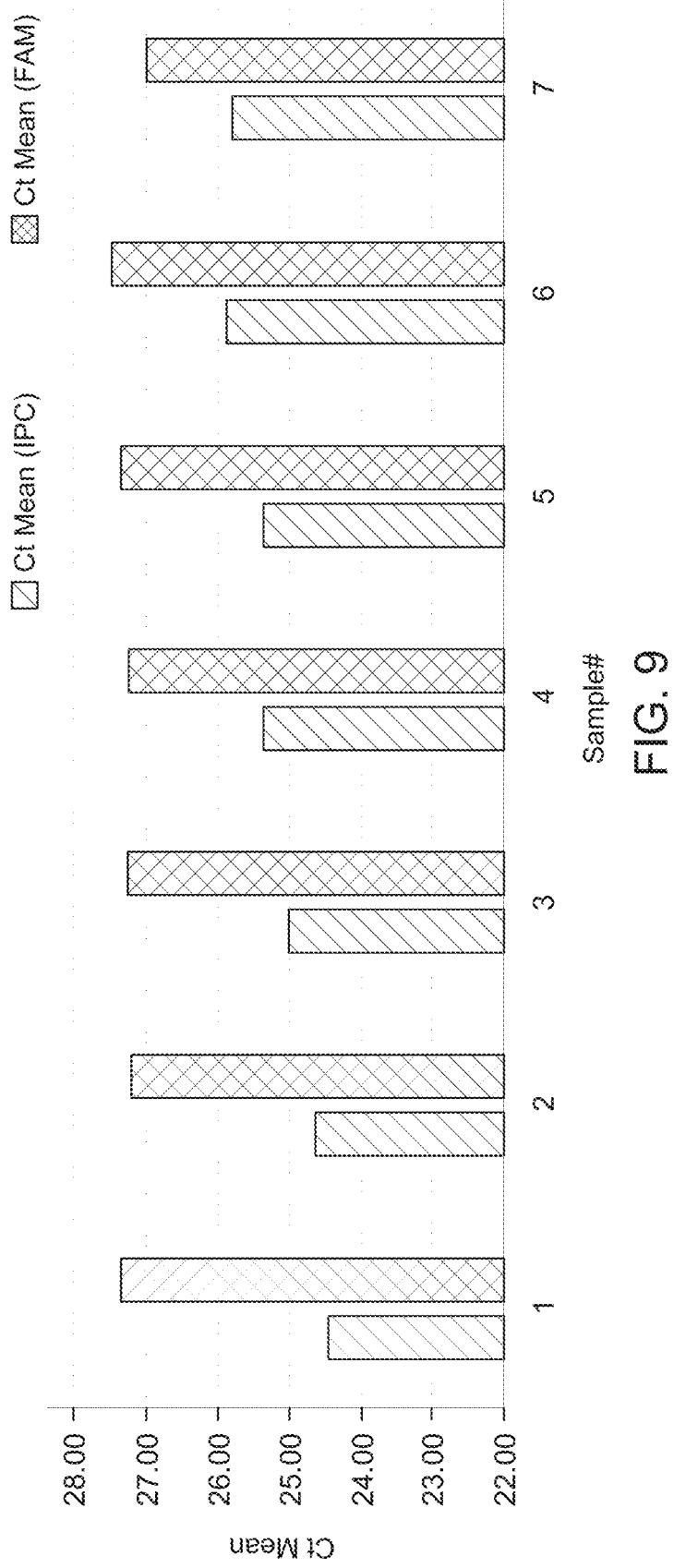
FIG. 9 is a graph showing polymerase chain reaction (PCR) performance of a biological sample following irradiation, in accordance with aspects of the present disclosure.

FIG. 9 illustrates polymerase chain reaction (PCR) performance of the biological sample 12 following irradiation of the photodegradable polymer, here polyhydroxyethyl methacrylate-NBS (PHEMA-NBS), at particular irradiation intervals and with different light sources. The graph and corresponding table (below) illustrate that PCR performance remains uninhibited in all the cases, including control samples with no photodegradable polymer, non-irradiated samples, and UV irradiated samples.

todegradable polymer 42 has a positive charge. This positive charge may enable the photodegradable polymer 42 to adhere or bind to the biological sample 28 when contacted or interfaced with the biological sample 28. Additionally or alternatively, the photodegradable polymer 42 may adhere or bind to the biological sample 28 through hydrogen bonding, or any other suitable adherence technique. In some embodiments, the photodegradable polymer 42 may be a hydrophobic polymer or a combination of one or more hydrophobic polymers.

Figure 10A:
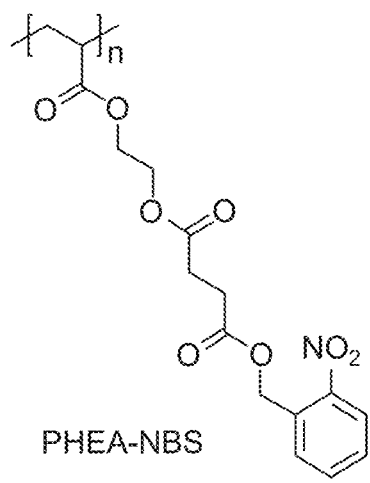
FIGS. 10A-10E show examples of photodegradable polymers that may be used in a photodegradable sample collection device, in accordance with aspects of the present disclosure.
Figure 10B:
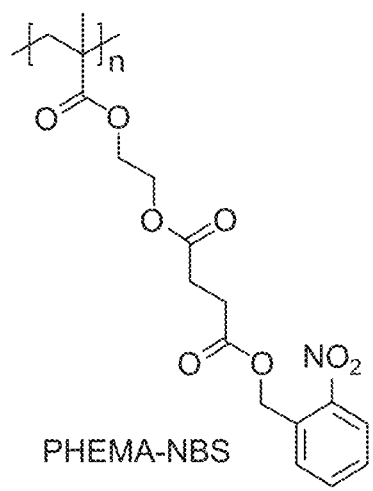
Figure 10C:
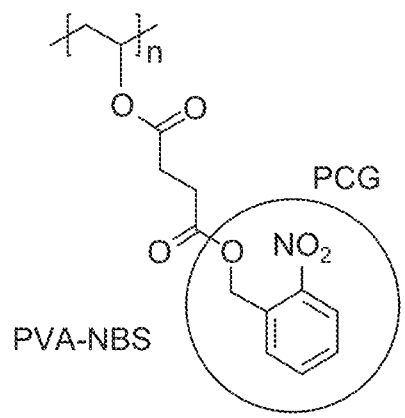
Figure 10D:
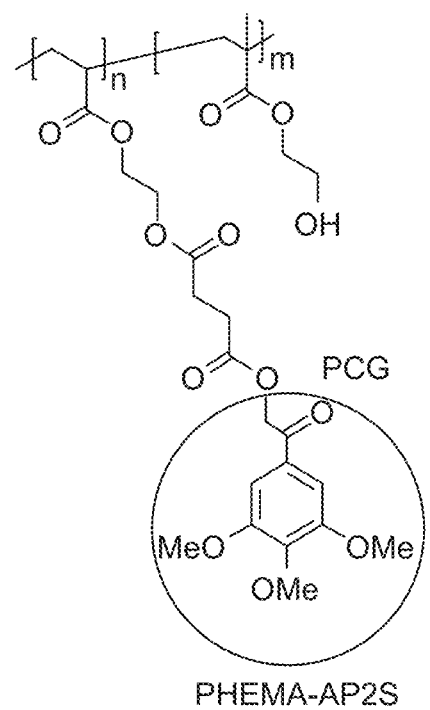
Figure 10E:
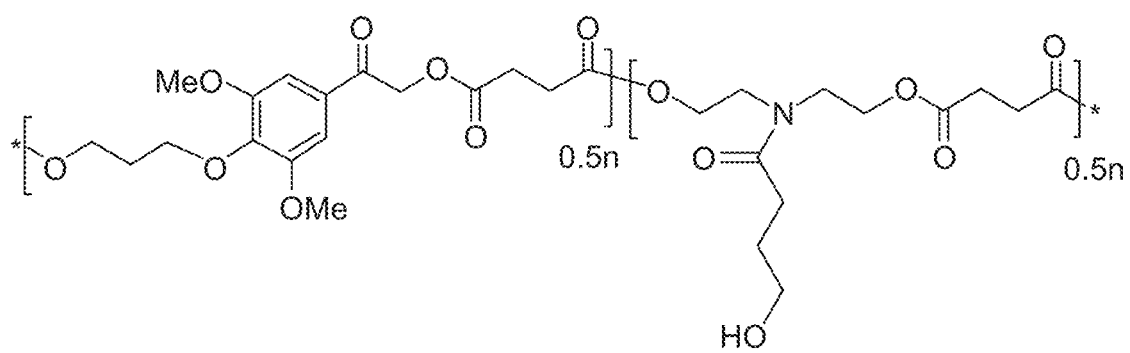

In some embodiments, the photodegradable polymer 42 may include photodegradable moieties or attached pendant groups. Examples of the photodegradable polymer 42 include polyhydroxyethyl acrylate (PHEA) (FIG. 10A), polyhydroxyethyl methacrylate (PHEMA) (FIG. 10B), and polyvinyl alcohol (PVA) each conjugated with nitrobenzyl succinate (NBS) or trimethoxyphenyl succinate (AP2S) as a pendant groups (FIG. 10D). The pendant group may be photodegradable such that it is susceptible to cleavage upon exposure to light. In some embodiments, the backbone of the photodegradable polymer 42 may include photocleavable moieties (e.g., alkoxyphenacyl polymer). The photocleavable moieties may be susceptible to cleavage upon exposure to light. In this manner, exposure to irradiation may break down the backbone of the photodegradable polymer 42 or cleave the photocleavable pendant groups, thus degrading the photodegradable polymer into the polymer, monomer, and/or oligomer pieces 48 of the photodegradable polymer

| PCR Sample# | Irradiation condition | Experiment Description | IPC - internal control | Report gene |
|---|---|---|---|---|
| 1 | n/a | 10 ng DNA + water, positive control | 24.49 | 27.34 |
| 2 | LED/365 nm/30 min, | irradiated, then add DNA 10 ng | 24.64 | 27.21 |
| 3 | LED/385 nm/30 min | irradiated, then add DNA 10 ng | 25.05 | 27.25 |
| 4 | Rayonet/365 nm/30 min | irradiated, then add DNA 10 ng | 25.40 | 27.23 |
| 5 | LED/365 nm/30 min, | premix 10 ng DNA, then irradiated | 25.41 | 27.34 |
| 6 | LED/385 nm/30 min | premix 10 ng DNA, then irradiated | 25.87 | 27.49 |
| 7 | Rayonet/365 nm/30 min | premix 10 ng DNA, then irradiated | 25.79 | 26.96 |
| 8 | n/a | water only, negative control | 24.57 | Undetermined |

FIGS. 10A-10E illustrate the structures of examples of the photodegradable polymer 42 that may be used to make up or coat the sample binding surface 13 of the photodegradable sample collection device 12. As previously discussed, the photodegradable sample collection device 12 and/or the sample binding surface 13 of the photodegradable sample collection device 12 may be made of the photodegradable polymer 42. The photodegradable polymer 42 may make up the whole of the photodegradable sample collection device 12, a portion of the photodegradable sample collection device 12, or a coating of all of part of the photodegradable sample collection device 12. In some embodiments, the sample binding surface 13 of the photodegradable polymer 42 may be a coating used to coat a traditional collection device, such as a cotton swab.

As previously discussed, the photodegradable polymer 42 may be a polymer that is susceptible to degradation or cleavage upon exposure to light, such that the backbone of the photodegradable polymer 42 is cleaved at photodegradable moieties or hydrophobic photocleavable pendant groups are cleaved off of the backbone of the photodegradable polymer. Additionally, the photodegradable polymer 42 may be a polymer that may adhere to or bind with the biological sample 28 (e.g., cells, DNA, RNA) to absorb or capture the biological sample 28 from the region of interest. For example, in some embodiments, the photodegradable polymer 42 may be a cationic polymer such that the pho-

42. In some embodiments, the photodegradable polymer 42 may have a molecular weight within the range of 10 kilodaltons (kDa)-1 megadalton (MDa). In some embodiments, the photodegradable polymer 42 may have a molecular weight within the range of 50 kDa-300 kDa. In some embodiments, the photodegradable polymer 42 may be spun via an electrospinning technique to form fibers, and the sample binding surface 13 may be made of the fibers of the photodegradable polymer 42, similar to cotton fibers of a cotton swab or cotton pad, or coated with the fibers of the photodegradable polymer 42.

Technical effects of the disclosed embodiments include a photodegradable sample collection device and system that may be used for capture and release of trace biological samples. The sample binding surface of the photodegradable sample collection device may be made of a photodegradable polymer, or a combination of one or more polymers. The photodegradable polymer may absorb or bind the biological sample when contacted with the biological sample. The photodegradable nature of the photodegradable polymer may enable the photodegradable polymer to be broken down in the presence of a particular wavelength, or range of wavelengths, of light into smaller polymer, monomer, and/or oligomer pieces that may be water soluble and may dissolve in the solution. This break down and dissolution of the photodegradable polymer may release the absorbed or bound biological sample, which may then be isolated and eluted from the solution for amplification and/or analysis. The photodegradable polymer of the photodegradable sample collection device may enable increased recovery of trace biological samples and a decrease in degradation of the biological sample in the process of capture and release. Further, the photodegradable sample collection device may be in a variety of forms, such as swabs, pads, brushes, or paper, thus enabling biological sample collection in a variety of formats. Additionally, the disclosed embodiments may include a photodegradable sample collection kit that may include any or all of the materials (e.g., photodegradable sample collection system) for capture and release of trace biological samples using the photodegradable sample collection device.

This written description uses examples to disclose the concepts discussed herein, including the best mode, and also sufficient disclosure to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method, comprising:
providing a biological sample;
providing a sample collection device, wherein the sample collection device comprises a sample binding surface comprising a photodegradable polymer configured to bind the biological sample, wherein the sample binding surface or a coating of the sample collection device comprises fibers comprising the photodegradable polymer wherein the fibers are between 1 nanometer and 20 micrometers in thickness;
contacting the biological sample with the sample binding surface of the sample collection device;
irradiating the sample binding surface and the bound biological sample using light emitted from a light source to initiate degradation of the photodegradable polymer of the sample binding surface to cause release of the biological sample, wherein the light comprises light of a wavelength between 300 nanometers and 700 nanometers.

2. The method of claim 1, wherein the photodegradable polymer comprises one or more hydrophobic polymers.

3. The method of claim 1, wherein the photodegradable polymer is water insoluble in polymer form.

4. The method of claim 1, wherein the degradation of the photodegradable polymer comprises cleaving one or more photocleavable moieties of the photodegradable polymer to break the photodegradable polymer into a plurality of polymers, monomers, oligomers, or a combination thereof, wherein the plurality of polymers, monomers, oligomers, or a combination thereof is water soluble.

5. The method of claim 4, further comprising:
contacting the sample binding surface and the bound biological sample with a solution before initiating the degradation, wherein the plurality of polymers, monomers, oligomers, or a combination thereof are released into the solution; and
isolating the biological sample from the solution.

6. The method of claim 1, wherein the sample binding surface or a coating of the sample collection device comprises fibers comprising the photodegradable polymer, wherein the fibers are created by electrospinning.

7. The method of claim 1, wherein the light is of a wavelength between 350 nm and 380 nm.

8. The method of claim 1, wherein the sample collection device comprises one of a swab, a pad, a brush, or a piece of paper.

* * * * *